(12) United States Patent
Martinez et al.

(10) Patent No.: US 9,963,423 B2
(45) Date of Patent: May 8, 2018

(54) SYNTHESIS OF 4-AMINO-2, 4-DIOXOBUTANOIC ACID

(71) Applicant: Millennium Enterprises, Inc., Marietta, GA (US)

(72) Inventors: Rodolfo Antonio Martinez, Santa Fe, NM (US); David Rembert Glass, Santa Fe, NM (US); Nathan Philip Martinez, Santa Fe, NM (US)

(*) Notice: Subject to any disclaimer, the term of this patent is extended or adjusted under 35 U.S.C. 154(b) by 0 days. days.

(21) Appl. No.: 15/404,900

(22) Filed: Jan. 12, 2017

(65) Prior Publication Data

US 2017/0197908 A1 Jul. 13, 2017

Related U.S. Application Data

(60) Provisional application No. 62/277,787, filed on Jan. 12, 2016, provisional application No. 62/445,488, filed on Jan. 12, 2017.

(51) Int. Cl.
*C07C 229/00* (2006.01)
*C07C 231/14* (2006.01)

(52) U.S. Cl.
CPC ................... *C07C 231/14* (2013.01)

(58) Field of Classification Search
CPC .... C07C 229/22; C07C 255/07; C07C 255/17
USPC ....................................................... 562/567
See application file for complete search history.

(56) References Cited

U.S. PATENT DOCUMENTS

| | | |
|---|---|---|
| 3,899,585 A | 8/1975 | Misato et al. |
| 4,336,397 A | 6/1982 | Cragoe, Jr. et al. |
| 5,922,649 A | 7/1999 | Pehu et al. |
| 6,083,876 A | 7/2000 | Jokinen et al. |
| 6,288,240 B1 | 9/2001 | Martinez et al. |
| 6,329,571 B1 | 12/2001 | Hiei |
| 6,448,202 B1 | 9/2002 | Miyazawa et al. |
| 6,555,500 B1 | 4/2003 | Unkefer et al. |
| 6,593,275 B1 | 7/2003 | Unkefer et al. |
| 6,703,346 B2 | 3/2004 | Herold et al. |
| 6,767,865 B2 | 7/2004 | Den Tandt et al. |
| 6,803,345 B2 | 10/2004 | Herold et al. |
| 6,831,040 B1 | 12/2004 | Unkefer et al. |
| 6,906,004 B2 | 6/2005 | Parrish et al. |
| 7,001,869 B2 | 2/2006 | Johnson |
| 7,094,735 B2 | 8/2006 | Herold et al. |
| 7,776,790 B2 | 8/2010 | Herold et al. |

(Continued)

FOREIGN PATENT DOCUMENTS

| | | |
|---|---|---|
| EP | 1095565 A1 | 5/2001 |
| EP | 1647181 A1 | 4/2006 |

(Continued)

OTHER PUBLICATIONS

Meister, A., Preparation and Enzymatic Reactions of the Keto Analogues of Asparagine and Glutamine, J. Biol. Chem. (1953) 200:571-589.

(Continued)

*Primary Examiner* — Deborah D Carr
(74) *Attorney, Agent, or Firm* — Kevin Soules; Luis M. Ortiz; Kermit D. Lopez

(57) ABSTRACT

A synthesis method comprises opening an anhydride to a 4-carbon acid-amide, removing ethanol soluble products, treating the resulting 4-amino-2-methylene-4-oxo-butanoic acid with Ozone in water, and evaporating the ozonolysis products to synthesize 4-amino-2,4-dioxobutanoic acid.

20 Claims, 12 Drawing Sheets

(56) References Cited

U.S. PATENT DOCUMENTS

| | | |
|---|---|---|
| 8,551,917 B2 | 10/2013 | Unkefer et al. |
| 8,759,256 B2 | 6/2014 | Parrish et al. |
| 8,802,595 B2 | 8/2014 | Unkefer et al. |
| 9,045,392 B2 | 6/2015 | Unkefer et al. |
| 2003/0032149 A1 | 2/2003 | Lalonde |
| 2003/0144147 A1 | 7/2003 | Herold et al. |
| 2003/0148889 A1 | 8/2003 | Herold et al. |
| 2003/0153461 A1 | 8/2003 | Parrish et al. |
| 2003/0153462 A1 | 8/2003 | Herold et al. |
| 2004/0063582 A1 | 4/2004 | Johnson |
| 2004/0127364 A1 | 7/2004 | Herold et al. |
| 2004/0132621 A1 | 7/2004 | Frisch et al. |
| 2004/0209777 A1 | 10/2004 | Gemma et al. |
| 2005/0137091 A1 | 6/2005 | Herold et al. |
| 2005/0170967 A1 | 8/2005 | Parrish et al. |
| 2005/0232868 A1 | 10/2005 | Rennie et al. |
| 2006/0090219 A1 | 4/2006 | Kisaka |
| 2006/0205601 A1 | 9/2006 | Herold et al. |
| 2007/0105719 A1 | 5/2007 | Unkefer et al. |
| 2010/0184599 A1 | 7/2010 | Parrish et al. |
| 2012/0090365 A1 | 4/2012 | Ersek et al. |
| 2014/0038824 A1 | 2/2014 | Unkefer et al. |

FOREIGN PATENT DOCUMENTS

| | | |
|---|---|---|
| JP | S4629767 | 8/1971 |
| JP | 10059808 | 3/1998 |
| JP | 2005512963 | 5/2005 |
| RU | 2277323 C1 | 6/2006 |
| RU | 2333245 C2 | 9/2008 |
| WO | 0154500 A1 | 8/2001 |
| WO | 03026422 A1 | 4/2003 |
| WO | 03026429 A1 | 4/2003 |
| WO | 2004054360 A2 | 7/2004 |
| WO | 2007056409 A2 | 5/2007 |

OTHER PUBLICATIONS

Nianjo, T. et al., Biological functions of proline in morphogenesis and osmotolerance revealed in antisense transgenic Arabidopsis thaliana, The Plant Journal (1999) 18(2):185-193.

Rooney, C. S. et al., Inhibitors of Glycoclic Acid Oxidase. 4-Substituted 3-Hydroxy-1H-pyrrole-2,5-dione Derivatives, J. Med. Chem. (1983) 26:700-714.

Stephani, R. A. et al. Structure of the Dimeric alpha-Keto Acid Analogue of Asparagine, The Journal of Biological Chemistry (1971) 246(22):7115-7118.

Ta, T. C. et al., Utilization of the Amide Groups of Asparagine and 2-Hydroxysuccinamic Acid by Young Pea Leaves, Plant Physiol. (1984) 75:527-530.

Tomassini, J. et al., Inhibition of Cap (m7GpppXm)-Dependent Endonuclease of Influenza Virus by 4-Substituted 2,4-Dioxobutanoic Acid Compounds, Antimicrobial Agents and Chemotherapy (1994) 38(12):2827-2837.

Verbic, T. Z. et al., An LFER study of the protolytic equilibria of 4-aryl-2,4-dioxobutanoic acids in aqueous solutions, J. Serb. Chem. Soc. (2007) 72(12)1201-1216.

Walkey, D. G. A., et al., The Inactivation of Virus in Cultured Shoot Tips of Nicotiana rustica L., J. Gen. Virol. (1969) 5:237-241.

SYNTHESIS OF 4-AMINO-2, 4-DIOXOBUTANOIC ACID

CROSS REFERENCE TO RELATED PATENT APPLICATIONS

This patent application claims the priority and benefit under 35 U.S.C. § 119(e) of U.S. Provisional Patent Application Ser. No. 62/277,787 filed Jan. 12, 2016, entitled "Improved Synthesis of 4-Amino-2, 4-Dioxobutanic Acid." U.S. Provisional Patent Application Ser. No. 62/277,787 is herein incorporated by reference in its entirety.

This patent application also claims the priority and benefit under 35 U.S.C. § 119(e) of U.S. Provisional Patent Application Ser. No. 62/445,488 filed Jan. 12, 2017, entitled "Synthesis of 4-Amino-2, 4-Dioxobutanic Acid." U.S. Provisional Patent Application Ser. No. 62/445,488 is herein incorporated by reference in its entirety

TECHNICAL FIELD

Embodiments are generally related to processes for the synthesis of the compound 4-amino-2,4-dioxobutanoic acid.

BACKGROUND

The compound 4-amino-2,4-dioxobutanoic acid is a metabolite found in plants. The compound has been prepared by the use of snake venom on asparagine. Production of 4-amino-2,4-dioxobutanoic acid by this method has been done on a small scale and is too expensive for commercial applications. Meister reported the synthesis in "Preparation and Enzymatic Reactions of the Keto Analogues of Asparagine and Glutamine," J. Biol. Chem., vol. 200, (1953), pp. 571-589.

The compound has also been produced by the reaction of ethyl cyanoacetate and diethyl oxalate to produce diethyl-2-cyano-3-hydroxybutenedioate using a series of acidic hydrolyses steps. However, such prior art processes are highly labor intensive.

Prior art methods of forming this compound required large volumes of solvents and large reaction vessels. In addition, such processes are very labor intensive. Accordingly, there is a need in the art for a new synthesis that would allow for large scale production of 4-amino-2,4-dioxobutanoic acid.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the disclosed embodiments to provide methods, processes, and/or systems for the synthesis of 4-amino-2,4-dioxobutanoic acid.

The aforementioned aspects and other objectives arid advantages can now be achieved as described herein. In one embodiment, a synthesis method comprises: opening an anhydride to a 4-carbon acid-amide; removing ethanol soluble products; treating the resulting 4-amino-2-methylene-4-oxo-butanoic acid with ozone in water; and evaporating the ozonolysis products to synthesize 4-amino-2,4-dioxobutanoic acid.

In another embodiment, a synthesis method comprises adding an itaconic anhydride to ammonium hydroxide, acidifying the solution to precipitate 4-amino-2-methylene-4-oxo-butanoic acid, filtering the precipitate, and introducing nitrogen to remove formaldehyde and thereby synthesize 2-Ketosuccinamic acid potassium salt.

BRIEF DESCRIPTION OF THE FIGURES

The accompanying figures, in which like reference numerals refer to identical or functionally similar elements throughout the separate views and are incorporated in and form a part of the specification, further illustrate aspects of the embodiments and, together with the background, brief summary, and detailed description, serve to explain the principles of the embodiments.

DETAILED DESCRIPTION

The particular values and configurations discussed in these non-limiting examples can be varied and are cited merely to illustrate at least one embodiment and are not intended to limit the scope thereof. The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The embodiments disclosed herein provide a new synthesis that allows for the large-scale production of 4-amino-2, 4-dioxobutanoic acid developed using dihydro-3-methylene-2,5-furandione (2-methylene-succinic anhydride, or itaconic acid).

Figure 1:
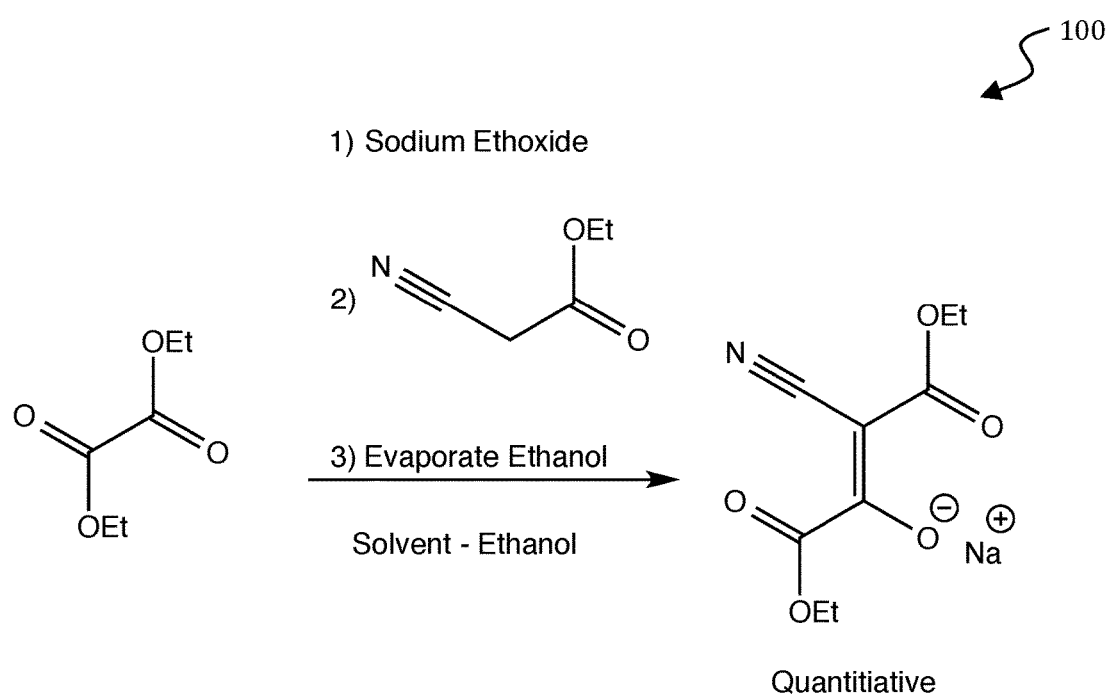
FIG. 1 depicts a diagram illustrating a reaction that assembles diethyl-2-cyano-3-hydroxybutenedioate, a precursor to the carbon skeleton of 4-amino-2,4-dioxobutanoic acid, from diethyl oxalate and ethyl cyanoacetate.

FIG. 1 depicts a schematic diagram 100 illustrating a reaction that assembles diethyl-2-cyano-3-hydroxybutenedioate, a precursor, to the carbon skeleton of 4-amino-2,4-dioxobutanoic acid, from diethyl oxalate and ethyl cyanoacetate.

Figure 2:
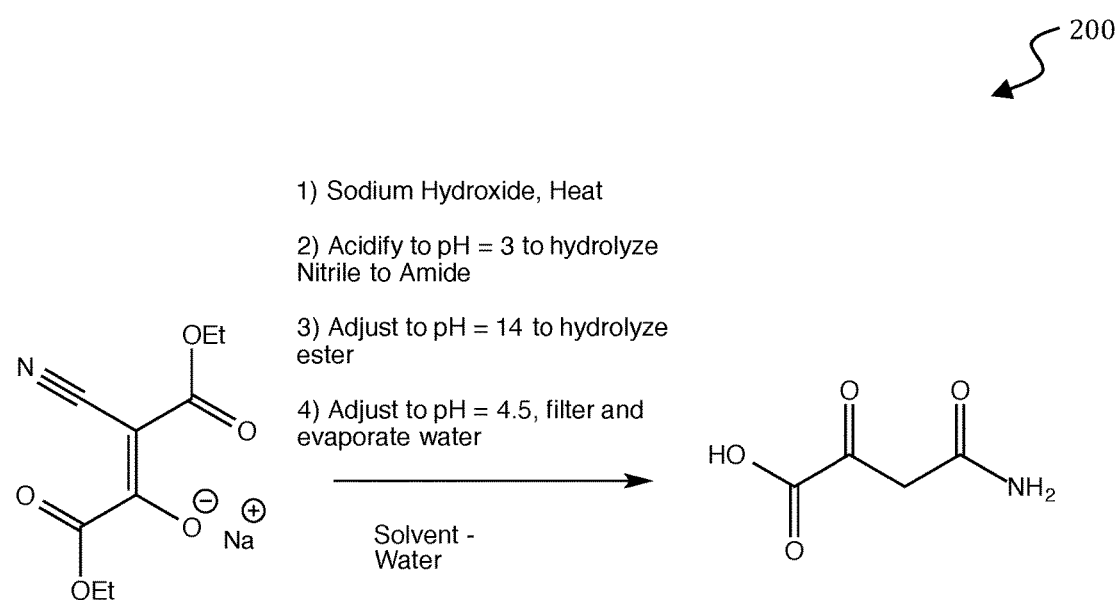
FIG. 2 depicts a diagram outlining a series of basic and acidic hydrolysis steps for converting diethyl-2-cyano-3-hydroxybutenedioate to 4-amino-2,4-dioxobutanoic acid, in accordance with an embodiment.

FIG. 2 depicts a diagram 200 outlining a series of basic and acidic hydrolysis steps used to convert diethyl-2-cyano-3-hydroxybutenedioate to 4-amino-2,4-dioxobutanoic acid as described in U.S. Pat. No. 9,045,392 titled "Preparation of 4-Amino-2,4-Dioxobutanoic Acid." U.S. Pat. No. 9,045,392 is herein incorporated by reference in its entirety.

Figure 3:
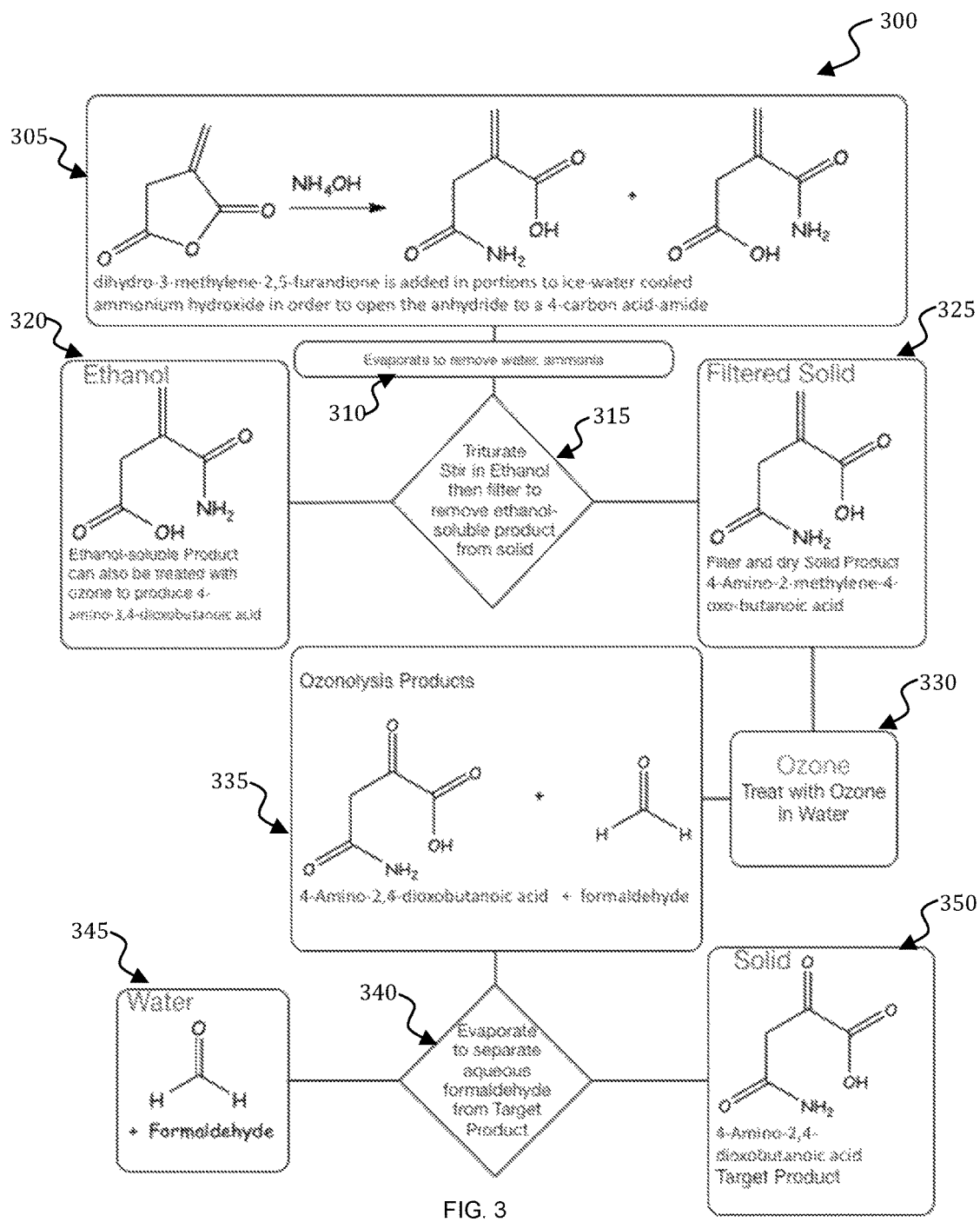
FIG. 3 depicts a flow chart illustrating steps associated with a method for synthesizing 4-amino-2,4-dioxobutanoic acid. which can be implemented in accordance with the disclosed embodiments.

FIG. 3 illustrates steps associated with a method 300 for synthesizing 4-amino-2,4-dioxobutanoic acid for large scale production, in accordance with an embodiment of the invention. At step 305, dihydro-3-methylene-2,5-furandione is added in portions to cooled ammonium hydroxide. In certain embodiments, the ammonium hydroxide can be cooled with ice water. This step opens the anhydride to a 4-carbon acid-amide.

At step 310, evaporation is used to remove the water and ammonia. As illustrated at step 315, the compound is triturated. Ethanol can also be added. Preferably, the Ethanol is added via stirring. Filtration can be used to remove the ethanol-soluble products from the solid.

The resulting ethanol-soluble product can also be treated with ozone to produce 4-amino-3, 4-dioxobutanoic acid as shown at step 320. As illustrated at step 325, the solid product can next be filtered and dried. The filtered and dried solid 4-amino-2-methylene-4-oxo-butanoic acid is then treated with ozone in water at step 330. This results in ozonolysis products 4-amino-2, 4-dioxobutanoic acid and formaldehyde as illustrated at step 335.

The resulting 4-amino-2, 4-dioxobutanoic acid and formaldehyde is evaporated at step 340 to separate the aqueous formaldehyde from the target product. As shown, the evaporation results in a water and formaldehyde byproduct as shown at step 345, and a solid 4-amino-2,4-dioxobutanoic acid as shown at step 350. The solid 4-amino-2,4-dioxobutanoic acid is the target product.

Figure 4:
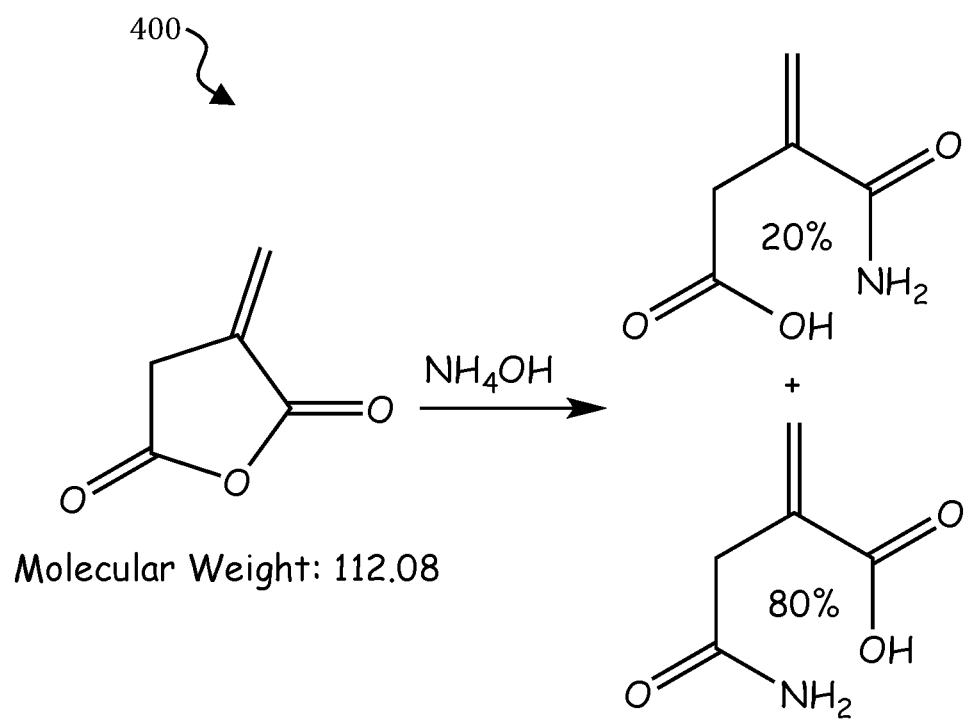
FIG. 4 depicts a diagram depicting the reaction of dihydro-3-methylene-2,5-furandione with aqueous ammonia in order to open the anhydride producing 4-amino-2-methylene-4-oxo-butanoic acid, the 4-carbon acid-amide carbon skeleton in accordance with the disclosed embodiments.

FIG. 4 illustrates a schematic diagram 400 depicting the reaction of dihydro-3-methylene-2,5-furandione with aqueous ammonia. This reaction can be used to open the anhydride producing 4-amino-2-methylene-4-oxo-butanoic acid, which is the 4-carbon acid-amide carbon skeleton of the present embodiments.

In an exemplary embodiment, ammonium hydroxide (28%, 157 mL, 2.3 moles) can be placed in a 1 Liter—3-neck Morton flask. The flask can be placed in an ice bath to cool the solution to 3° C. Once cooled, dihydro-3-methylene-2,5-furandione (102 g, 0.9099 moles) can be added in 5 gram portions as a solid in order to maintain the reaction temperature at or below 10° C. After the reaction is complete, the solution can be evaporated to near dryness and then additional water (50 mL) can be added and the solution can be evaporated again. This can be repeated until the pH of the aqueous solution tests to pH 4.5. At this point, ethanol (100 mL) can be added and the mixture can be evaporated to dry the product by azeotropic distillation. The resulting solid (117 grams, 99% yield) can be stirred in ethanol to separate the minor 4-amino-3-methylene-4-oxo-butanoic acid product, which is soluble in ethanol. The target 4-amino-2-methylene-4-oxo-butanoic acid solid product can be filtered and dried in a vacuum oven to yield 93 grams (80% yield) of a colorless solid. It should be understood that the amounts, sizes, and temperatures provided in this example are only intended to be illustrative and are not intended to limit the scope of the possible embodiments. Other amounts, sizes, and temperatures may be used in other embodiments.

Figure 5:
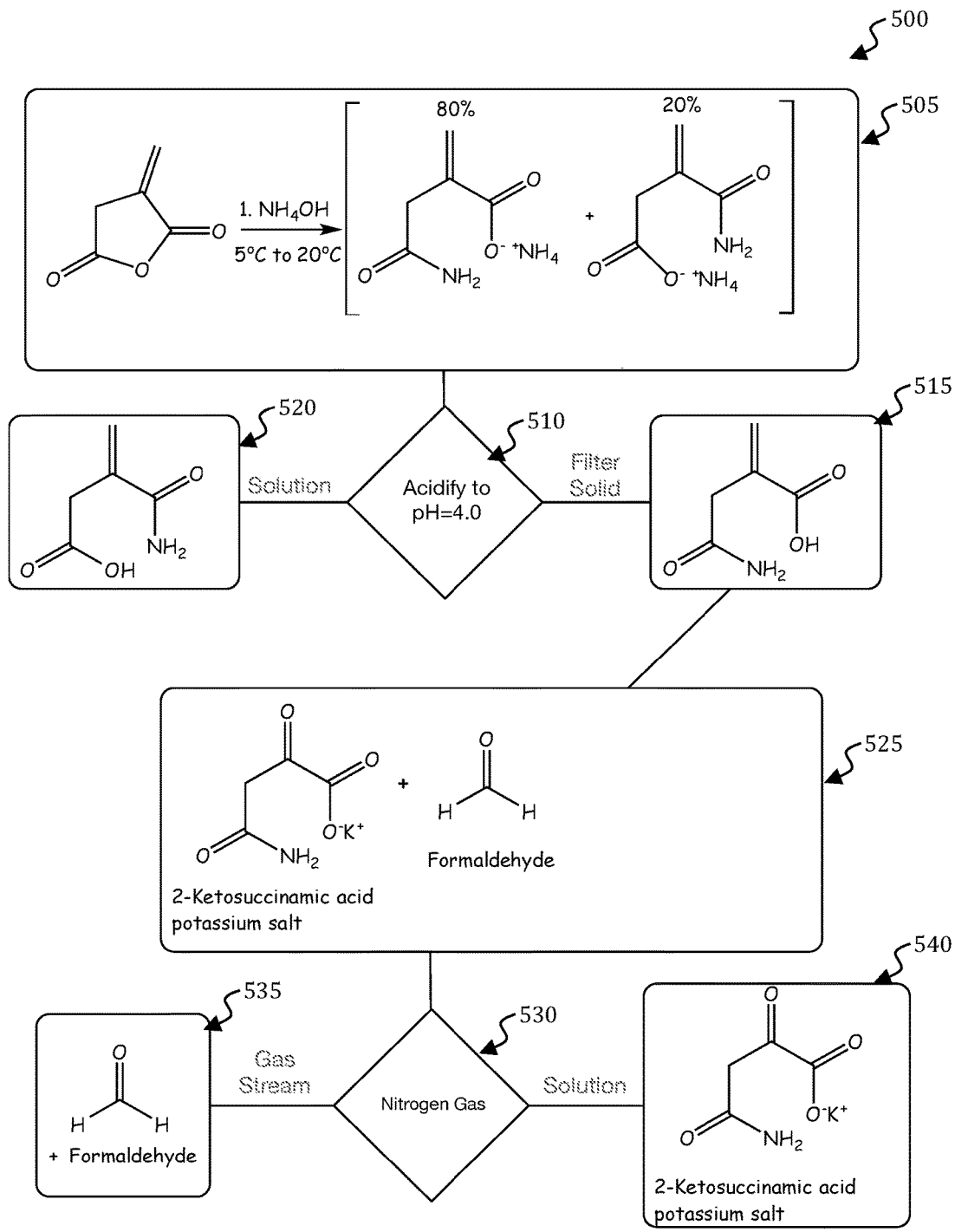
FIG. 5 depicts a flow chart illustrating steps associated with a method for synthesizing 2-Ketosuccinamic acid potassium salt, which can be implemented in accordance with the disclosed embodiments.

FIG. 5 illustrates a method 500 for synthesizing 4-amino-2,4-dioxobutanoic acid for large scale production, in accordance with an embodiment of the invention. At step 505, Itaconic Anhydried is added in portions until the necessary amount of reagent is added. Typically this step is competed in 8-10 additions while the reaction is maintained at 5-20 degrees C. It should be appreciated that additional or fewer additions may be required.

At step 510, the solution can he acidified to pH 4.0, using acid such as hydrochloric acid, to precipitate the major isomer. This results in a solution and a solid. The neutralized solution can be filtered leaving the filtered solid product s shown at step 515. The remaining solution is also shown at step 520.

Next at step 525, the product can be neutralized to pH 7.0 with KOH and treated with Ozone until the reaction is complete. This results is 2-Ketosuccinamic acid potassium salt and Formaldehyde. At step 530, nitrogen gas is passed through the solution to remove the Formaldehyde as a gas stream, shown at step 535. The remaining solution is 2-Ketosuccinamic acid potassium salt, illustrated at step 540.

In an exemplary embodiment of the method illustrated in FIG. 5, Ammonium hydroxide (28%, 2500 mL, 36.26 moles) can be placed in a 10 Liter reactor—3-neck Morton flask. The flask can be placed in an ice bath and the solution cooled to 3° C. At this point, dihydro-3-methylene-2,5-furandione (1502.7 g, 13.41 moles) can be added in 150 gram portions as the solid in order to maintain the reaction temperature at under 20° C. The complete addition can generally be accomplished in 3 hours.

After the reaction is complete, the cold solution is neutralized to pH 4.0 using hydrochloric acid (6M) to precipitate the major isomer (4-amino-2-methylene-4-oxo-butanoic acid) which is filtered to give 1344.1 g of product. The purity of the product at this stage is 98% and is suitable for application in the subsequent steps. The product is washed with water (2800 mL) to remove any ammonium chloride present in the solid. The 4-amino-2-methylene-4-oxo-butanoic acid (99% pure) has a mass of 1194.5 grams (69% yield). Again, it should be understood that the amounts, sizes, purities, and temperatures provided in this example are only intended to be illustrative and are not intended to limit the scope of the possible embodiments. Other amounts, sizes, purities, and temperatures may be used in other embodiments.

Figure 6:
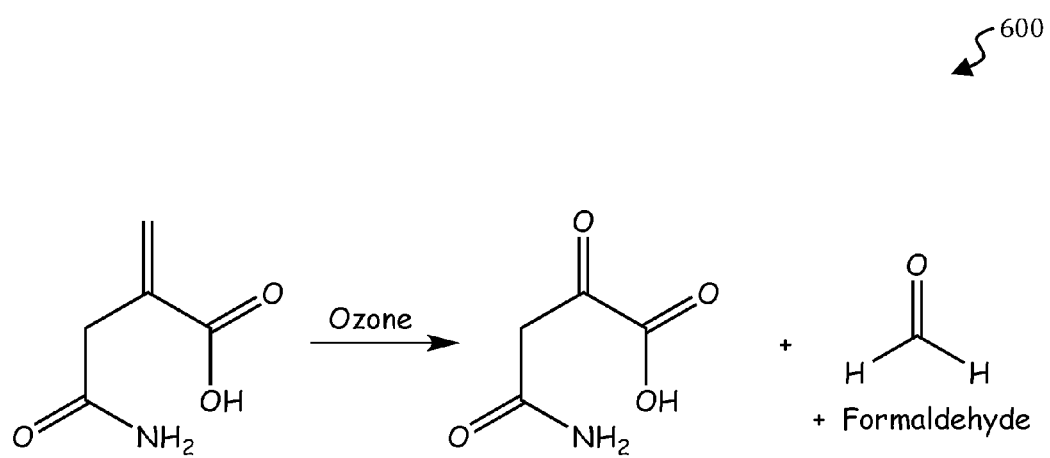
FIG. 6 depicts a schematic diagram illustrating the reaction of ozone with 4-amino-2-methylene-4-oxo-butanoic acid in water to produce 4-amino-2,4-dioxobutanoic acid, in accordance with an embodiment.

FIG. 6 depicts a schematic diagram 600 illustrating the reaction of ozone with 4-amino-2-methylene-4-oxo-butanoic acid in water to produce 4-amino-2,4-dioxobutanoic acid.

In an exemplary embodiment, 4-Amino-2-methylene-4-oxo-butanoic acid (3.99 g, 0.0309 moles) can be dissolved into water (50 mL). The homogenous colorless solution can be cooled in an RT water bath at a temperature of 20° C. Ozone can be bubbled through the solution at 1 L/min for a total of 90 minutes. After this period, nitrogen gas can be bubbled in the solution to remove excess ozone. The solution is evaporated and the formaldehyde co-distills with the water. NMR analysis shows that the expected 4-amino-2,4-dioxobutanoic acid product is formed in quantitative yield.

In further exemplary embodiments, 4-Amino-2-methylene-4-oxo-butanoic acid (e.g., 1035 g, 8.016 moles) can be dissolved into potassium hydroxide (e.g., 6M, 1200 mL). The homogenous colorless solution is cooled in an ice water bath. Ozone is bubbled at 2 liters/minute for 6.5 days. After this period, nitrogen gas is passed/bubbled in the, solution to remove excess ozone and formaldehyde. The solution is adjusted to 3.0 molar by the addition of water. The product can be used as this solution.

Again, it should be understood that the amounts, sizes, purities, and temperatures providedi in these exemplary embodiments are only intended to be illustrative and are not intended to limit the scope of the possible embodiments. Other amounts, sizes, purities, and temperatures may be used in other embodiments.

Nuclear magnetic resonance spectroscopy (NMR) data related to 4-Amino-2-methylene-4-oxo-butanoic acid, in accordance with the disclosed embodiments, is provided herein. The NMR analysis shows that the expected 4-amino-2,4-dioxobutanoic acid product is formed in quantitative yield.

Figure 7:
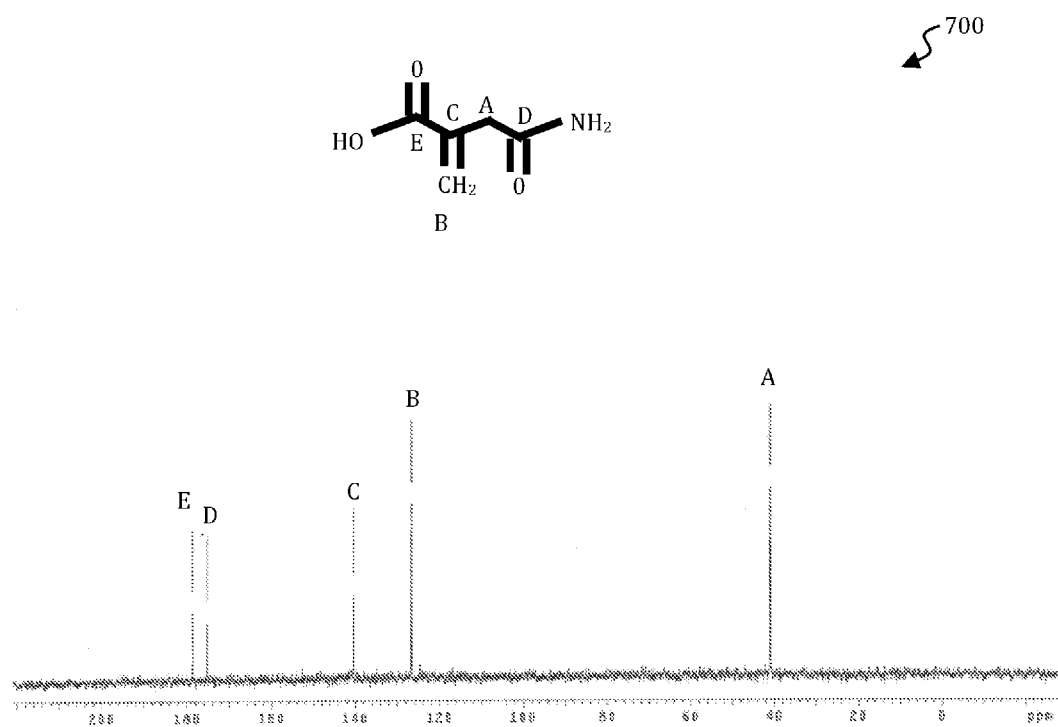
FIG. 7 illustrates a (Nuclear Magnetic Resonance) NMR, spectrum of 4-amino-2-methylene-4-oxo-butanoic acid in water prior to reaction with ozone, in accordance with an embodiment.
Figure 8:
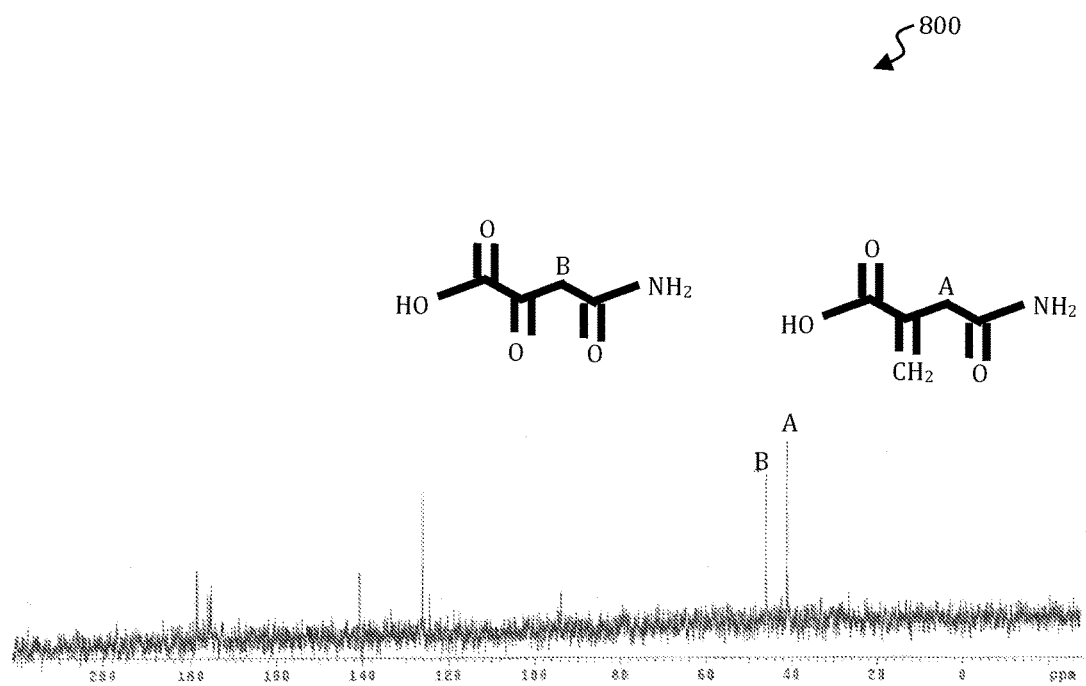
FIG. 8 depicts an NMR spectrum of 4-amino-2-methylene-4-oxo-butanoic acid in water after treatment with ozone, illustrating partial conversion of the 4-amino-2-methylene-4-oxo-butanoic acid to the products 4-amino-2,4-dioxobutanoic acid and formaldehyde, in accordance with an embodiment.

For example, FIG. 7 illustrates an NMR spectrum 700 of 4-amino-2-methylene-4-oxo-butanoic acid in water prior to reaction with ozone. FIG. 8 depicts an NMR spectrum 800 of 4-amino-2-methylene-4-oxo-butanoic acid in water after treatment with ozone for 35 minutes. This illustrates the partial conversion of the 4-amino-2-methylene-4-oxo-butanoic acid to the products 4-amino-2,4-dioxobutanoic acid and formaldehyde.

Figure 9:
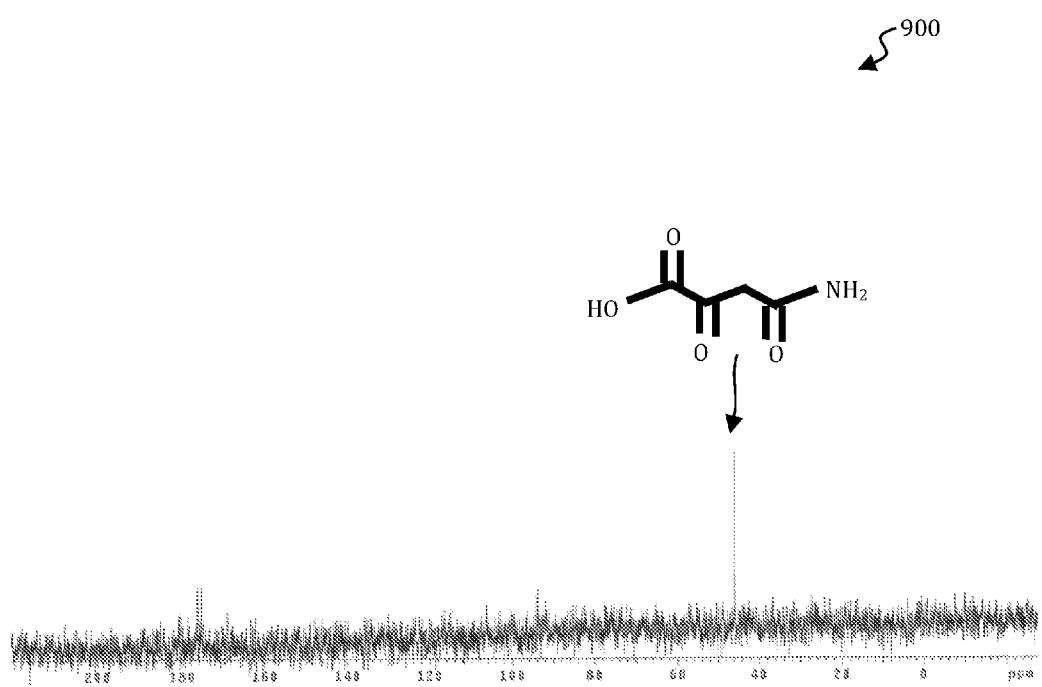
FIG. 9 depicts an NMR spectrum of 4-amino-2-methylene-4-oxo-butanoic acid in water after treatment with ozone, showing complete conversion of the 4-amino-2-methylene-4-oxo-hutanoic acid to the products 4-amino-2,4-dioxobutanoic acid and formaldehyde, in accordance with an embodiment.
Figure 10:
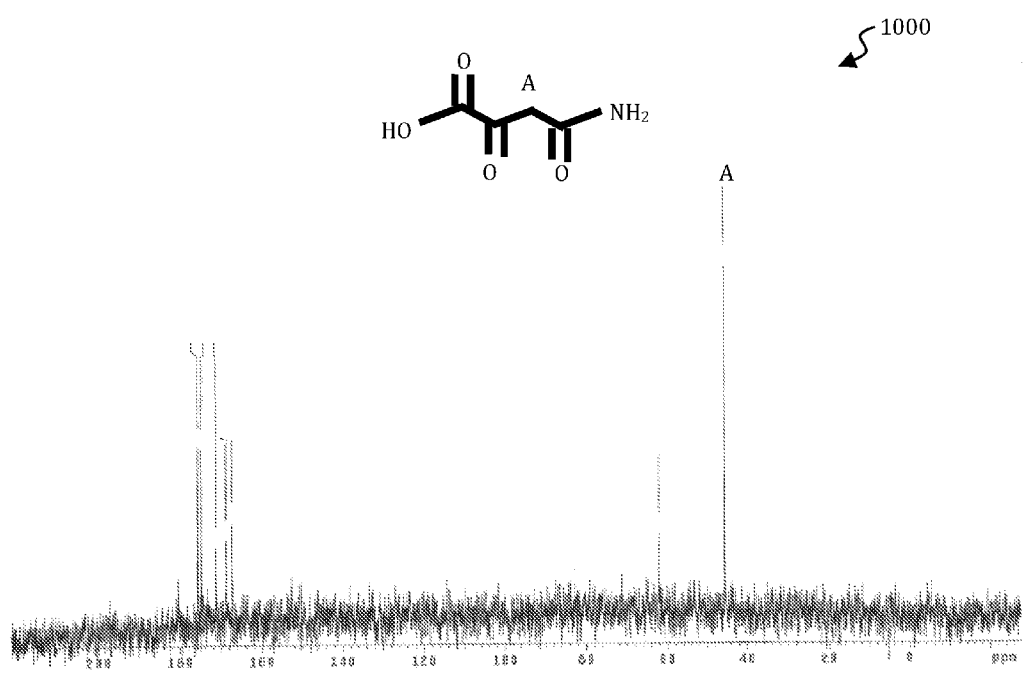
FIG. 10 depicts an NMR spectrum of 4-amino-2,4-dioxobutanoic acid in water, in accordance with an embodiment.

In FIG. 9, an NMR spectrum 900 of 4-amino-2-methylene-4-oxo-butanoic acid in water after treatment with ozone for 90 minutes is shown. This demonstrates complete conversion of the 4-amino-2-methylene-4-oxo-butanoic acid to the products 4-amino-2,4-dioxobutanoic acid and formaldehyde. FIG. 10 depicts an NMR spectrum 1000 of 4-amino-2,4-dioxobutanoic acid in water.

The synthesis of 4-amino-2,4-dioxobutanoic acid by the methods and processes disclosed herein provides a number of advantages. First, the starting material has the carbon structure already assembled thus avoiding the use of condensation chemistry to make the core structure. The starting material is also a readily available compound in metric ton quantities. Additionally, the methods and process described herein reduce the amount of solvent required, the final step uses ozone to produce the final product, and the waste stream for this process is greatly reduced.

Figure 11:
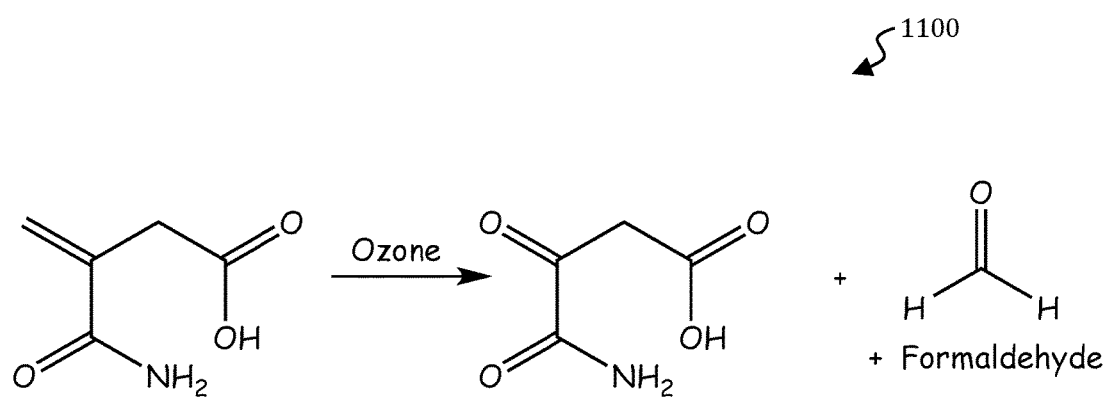
FIG. 11 depicts that the ethanol-soluble product, 4-amino-3-methylene-4-oxo-butanoic acid, which is also produced, can he treated with ozone to produce 4-amino-3,4-dioxobutanoic acid. in accordance with an embodiment.

It should be appreciated that the ethanol-soluble product, 4-amino-3-methylene-4-oxo-butanoic acid, also produced as illustrated above in FIG. 6, can be treated with ozone to produce 4-amino-3,4-dioxobutanoic acid. Thus, FIG. 11 depicts a schematic diagram 1100 illustrating that the ethanol-soluble product, 4-amino-3-methylene-4-oxo-butanoic acid, which is also produced, can be treated with ozone to produce 4-amino-3,4-dioxobutanoic acid.

Figure 12:
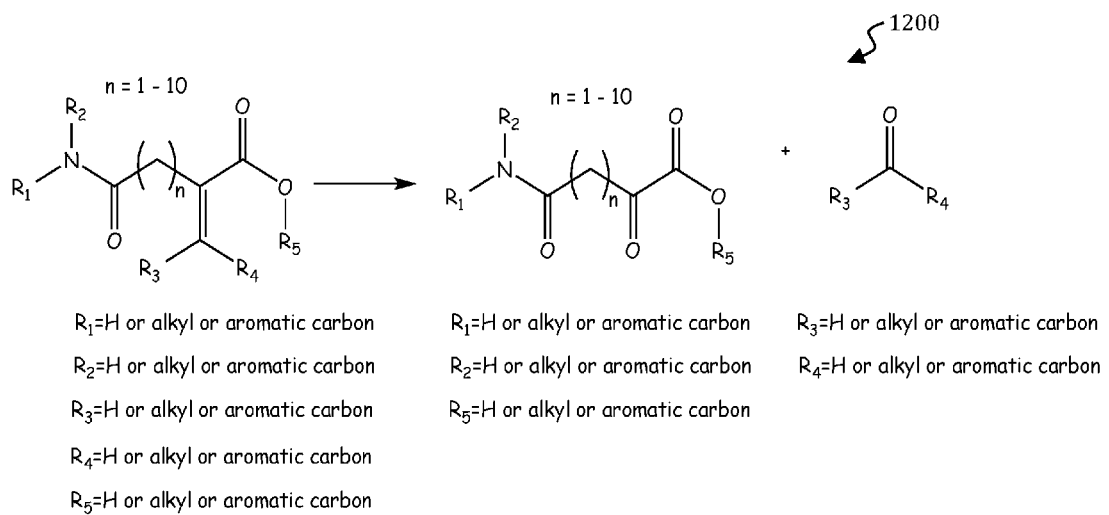
FIG. 12 shows a generic schematic diagram for the production of a 2-oxo-acid-amide having any length alkyl chain, in accordance with an embodiment.

It should be appreciated that, more generally, the above embodiments can be used to produce 2-oxo ester-amides. FIG. 12 illustrates that the above embodiments can be utilized as a general method to produce 2-oxo ester-amides and 2-oxo acid-amides. Specifically, in FIG. 12, a generalized diagram 1200 for the production of a 2-oxo-acid-amide having any length alkyl chain is shown. In this generic embodiment, n=1-10 carbons, R1 can be hydrogen, any alkyl, or aromatic group. R2 can be hydrogen, any alkyl, or aromatic group. R3 can be hydrogen, any alkyl, or aromatic group. R4 can be hydrogen, any alkyl, or aromatic group. R5 can be hydrogen, any alkyl, or aromatic group.

Based on the foregoing, it can be appreciated that a number of embodiments, preferred and alternative, are disclosed herein. For example, in one embodiment, a synthesis method comprises opening an anhydride to a 4-carbon acid-amide, removing ethanol soluble products, treating the resulting 4-amino-2-methylene-4-oxo-butanoic acid with Ozone in water, and evaporating the ozonolysis products to synthesize 4-amino-2,4-dioxobutanoic acid.

In an embodiment, opening the anhydride to a 4-carbon acid-amide further comprises adding dihodro-3-methylene-2,5-furandione to ammonium hydroxide. In an embodiment, adding dihodro-3-methylene-2,5-furandione to ammonium hydroxide further comprises cooling the ammonium hydroxide. In an embodiment, adding dihodro-3-methylene-2,5-furandione to ammonium hydroxide further comprises adding the dihodro-3-methylene-2,5-furandione to the ammonium hydroxide in pre-sized sub-portions.

In another embodiment. the synthesis method further comprises triturating the dihodro-3-methylene-2,5-furandione added to the ammonium hydroxide.

In an embodiment, removing ethanol soluble products further comprises filtering and drying 4-amino-2-methylene-4-oxo-butanoic acid. In an embodiment, the removed ethanol-soluble products are treated with ozone to produce 4-amino-3,4-dioxobutanic acid.

In another embodiment, the synthesis method further comprises drying the synthesized 4-amino-2,4-dioxobutanoic acid in a vacuum oven.

In yet another embodiment, a synthesis method comprises adding an itaconic anhydride to ammonium hydroxide, acidifying the solution to precipitate 4-amino-2-methylene-4-oxo-butanoic acid, filtering the precipitate, and introducing nitrogen to remove formaldehyde and thereby synthesize 2-Ketosuccinamic acid potassium salt.

In an embodiment, adding an itaconic anhydride to ammonium hydroxide further comprises maintaining a reaction of the itaconic anhydride to ammonium hydroxide between 5 degrees Celsius and 20 degrees Celsius. In another embodiment, adding an itaconic anhydride to ammonium hydroxide further comprises adding the itaconic anhydride in portions. In an embodiment, the portions comprise between 8 and 10 equal portions of the itaconic anhydride.

In an embodiment, acidifying the solution to precipitate 4-amino-2-methylene-4-oxo-butanoic acid further comprises acidifying the solution, using hydrochloric acid. In an embodiment, acidifying the solution to precipitate 4-amino-2-methylene-4-oxo-butanoic acid further comprises acidifying the solution to a pH of 4.0.

In an embodiment, the synthesis method further comprises neutralizing the solution to pH 7.0 with KOH, and treating the filtered precipitate with Ozone until a reaction is completed.

In another embodiment, the synthesis method further comprises washing the 4-amino-2-methylene-4-oxo-butanoic acid with water to remove any ammonium chloride. In an embodiment, removing formaldehyde further comprises removing a gas stream of water and formaldehyde.

In yet another embodiment, a synthesis method comprises adding dihodro-3-methylene-2,5-furandione to cooled ammonium hydroxide, triturating the dihodro-3-methylene-2,5-furandione added to the ammonium hydroxide, removing ethanol soluble products, treating the resulting 4-amino-2-methylene-4-oxo-butanoic acid with Ozone in water, and evaporating the ozonolysis products to synthesize 4-amino-2,4-dioxobutanoic acid. The synthesis method may further comprise drying the synthesized 4-amino-2,4-dioxobutanoic acid in a vacuum oven.

It will be appreciated that variations of the above-disclosed and other features and functions, or alternatives thereof, may be desirably combined into many other different systems or applications. Also, it can be appreciated that various presently unforeseen or unanticipated alternatives, modifications, variations or improvements therein may be subsequently made by those skilled in the art which are also intended to be encompassed by the following claims.

What is claimed is:

1. A synthesis method comprising:
   opening an anhydride to a 4-carbon acid-amide;
   removing ethanol soluble products;
   treating the resulting 4-amino-2-methylene-4-oxo-butanoic acid with Ozone in water; and
   evaporating the ozonolysis products to synthesize 4-amino-2,4-dioxobutanoic acid.

2. The synthesis method of claim 1 wherein opening said anhydride to a 4-carbon acid-amide further comprises:
   adding dihodro-3-methylene-2,5-furandione to ammonium hydroxide.

3. The synthesis method of claim 2 wherein adding dihodro-3-methylene-2,5-furandione to ammonium hydroxide further comprises:
   cooling said ammonium hydroxide.

4. The synthesis method of claim 2 wherein adding dihodro-3-methylene-2,5-furandione to ammonium hydroxide further comprises:
   adding said dihodro-3-methylene-2,5-furandione to said ammonium hydroxide in pre-sized sub-portions.

5. The synthesis method of claim 2 further comprising:
   triturating said dihodro-3-methylene-2,5-furandione added to said ammonium hydroxide.

6. The synthesis method of claim 1 wherein removing ethanol soluble products further comprises:
   filtering and drying 4-amino-2-methylene-4-oxo-butanoic acid.

7. The synthesis method of claim 1 wherein removed ethanol-soluble products are treated with ozone to produce 4-amino-3,4-dioxobutanic acid.

8. The synthesis method of claim 1 further comprising:
   drying said synthesized 4-amino-2,4-dioxobutanoic acid in a vacuum oven.

9. A synthesis method comprising:
   adding an itaconic anhydride to ammonium hydroxide;
   acidifying the solution to precipitate 4-amino-2-methylene-4-oxo-butanoic acid;
   filtering the precipitate; and
   introducing nitrogen to remove formaldehyde and thereby synthesize 2-Ketosuccinamic acid potassium salt.

10. The synthesis method of claim 9 wherein adding an itaconic anhydride to ammonium hydroxide further comprises:
    maintaining a reaction of said itaconic anhydride to ammonium hydroxide between 5 degrees Celsius and 20 degrees Celsius.

11. The synthesis method of claim 9 wherein adding an itaconic anhydride to ammonium hydroxide further comprises:
    adding said itaconic anhydride in portions.

12. The synthesis method of claim 11 wherein said portions comprise between 8 and 10 equal portions of said itaconic anhydride.

13. The synthesis method of claim 9 wherein acidifying the solution to precipitate 4-amino-2-methylene-4-oxo-butanoic acid further comprises:
    acidifying the solution using hydrochloric acid.

14. The synthesis method of claim 9 wherein acidifying the solution to precipitate 4-amino-2-methylene-4-oxo-butanoic acid further comprises:
    acidifying the solution to a pH of 4.0.

15. The synthesis method of claim 9 further comprising:
    neutralizing said solution to pH 7.0 with KOH.

16. The synthesis method of claim 9 further comprising:
    treating said filtered precipitate with Ozone until a reaction is completed.

17. The synthesis method of claim 9 further comprising:
    washing the 4-amino-2-methylene-4-oxo-butanoic acid with water to remove any ammonium chloride.

18. The synthesis method of claim 9 wherein removing formaldehyde further comprises:
    removing a gas stream of water and formaldehyde.

19. A synthesis method comprising:
    adding dihodro-3-methylene-2,5-furandione to cooled ammonium hydroxide;
    triturating said dihodro-3-methylene-2,5-furandione added to said ammonium hydroxide;
    removing ethanol soluble products;
    treating the resulting 4-amino-2-methylene-4-oxo-butanoic acid with Ozone in water; and
    evaporating the ozonolysis products to synthesize 4-amino-2,4-dioxobutanoic acid.

20. The synthesis method of claim 19 further comprising:
drying said synthesized 4-amino-2,4-dioxobutanoic acid in a vacuum oven.

\* \* \* \* \*